(12) United States Patent
Chiao (10) Patent No.: US 10,226,478 B2
(45) Date of Patent: Mar. 12, 2019

(54) DOSAGE REGIMEN FOR SAPACITABINE AND DECITABINE IN COMBINATION FOR TREATING ACUTE MYELOID LEUKEMIA

(75) Inventor: Judy H. Chiao, Berkeley Heights, NJ (US)

(73) Assignee: Cyclacel Limited, London (GB)

(*) Notice: Subject to any disclaimer, the term of this patent is extended or adjusted under 35 U.S.C. 154(b) by 176 days.

(21) Appl. No.: 14/111,430

(22) PCT Filed: Apr. 13, 2012

(86) PCT No.: PCT/GB2012/050815
§ 371 (c)(1),
(2), (4) Date: Dec. 17, 2013

(87) PCT Pub. No.: WO2012/140436
PCT Pub. Date: Oct. 18, 2012

(65) Prior Publication Data
US 2014/0094428 A1 Apr. 3, 2014

(30) Foreign Application Priority Data

| Apr. 14, 2011 | (GB) | 1106339.3 |
| Oct. 13, 2011 | (GB) | 1117693.0 |
| Dec. 8, 2011 | (GB) | 1121105.9 |

(51) Int. Cl.
*A61K 31/7068* (2006.01)
*A61K 31/706* (2006.01)

(52) U.S. Cl.
CPC ........ *A61K 31/7068* (2013.01); *A61K 31/706* (2013.01)

(58) Field of Classification Search
CPC .................. A61K 31/7068; A61K 31/706
See application file for complete search history.

(56) References Cited

U.S. PATENT DOCUMENTS

| 5,616,567 A | 4/1997 | Sasaki et al. |
| 5,654,420 A | 8/1997 | Matsuda et al. |
| 5,691,319 A | 11/1997 | Kaneko et al. |
| 5,824,984 A | 10/1998 | Morrow |
| 6,369,086 B1 | 4/2002 | Davis et al. |
| 6,462,063 B1 | 10/2002 | Ho et al. |
| 6,908,906 B2 | 6/2005 | Takita et al. |
| 7,772,207 B2 | 8/2010 | Green et al. |
| 8,124,593 B2 | 2/2012 | Gianella-Borradori et al. |
| 8,349,792 B2 | 1/2013 | Green et al. |
| 8,497,291 B2 | 7/2013 | Westwood et al. |
| 8,530,445 B2 | 9/2013 | Green et al. |
| 8,536,188 B2 | 9/2013 | Chiao |
| 8,884,001 B2 | 11/2014 | Wood et al. |
| 8,975,239 B2 | 3/2015 | Green et al. |
| 9,675,631 B2 | 6/2017 | Chiao |
| 2002/0156033 A1 | 10/2002 | Bratzler et al. |
| 2002/0161377 A1 | 10/2002 | Rabkin |
| 2002/0165569 A1 | 11/2002 | Ramzipoor et al. |
| 2003/0026801 A1 | 2/2003 | Weiner et al. |
| 2003/0087873 A1 | 5/2003 | Stuyver et al. |
| 2003/0124512 A1 | 7/2003 | Stuyver |
| 2003/0134827 A1 | 7/2003 | Duan et al. |
| 2004/0097461 A1 | 5/2004 | Sommadossi et al. |
| 2005/0009773 A1 | 1/2005 | Kandimalla et al. |
| 2005/0014716 A1 | 1/2005 | Wang et al. |
| 2005/0124532 A1 | 6/2005 | Sommadossi et al. |
| 2005/0171096 A1 | 8/2005 | Sheppeck et al. |
| 2006/0211369 A1 | 9/2006 | Steelberg et al. |
| 2009/0274773 A1 | 11/2009 | Green et al. |
| 2011/0028421 A1 | 2/2011 | Engel et al. |
| 2013/0196938 A1 | 8/2013 | Green et al. |
| 2014/0142058 A1 | 5/2014 | Chia |

FOREIGN PATENT DOCUMENTS

| CN | 101185629 A | 5/2008 |
| EP | 0535231 B1 | 4/1993 |
| EP | 0536936 A1 | 4/1993 |
| EP | 1364959 B1 | 11/2003 |
| EP | 1669364 A2 | 6/2006 |
| EP | 1736478 A1 | 12/2006 |
| WO | 01/97843 A2 | 12/2001 |
| WO | 02/28829 A2 | 4/2002 |
| WO | 02/32920 A2 | 4/2002 |
| WO | 02/46182 A1 | 6/2002 |
| WO | 02/064609 A1 | 8/2002 |
| WO | 03/039536 A1 | 5/2003 |
| WO | 2004091441 A2 | 10/2004 |
| WO | 2004103301 A2 | 12/2004 |
| WO | 2005000204 A2 | 1/2005 |
| WO | 2005/053699 A1 | 6/2005 |
| WO | 2006/090931 A1 | 8/2006 |
| WO | 2007054731 A1 | 5/2007 |
| WO | 2007/072061 A2 | 6/2007 |
| WO | 2007/132228 A1 | 11/2007 |
| WO | 2008/007113 A2 | 1/2008 |
| WO | 2008/132443 A1 | 11/2008 |
| WO | 2009/150405 A1 | 12/2009 |
| WO | 2012/140436 A1 | 10/2012 |

OTHER PUBLICATIONS

O'Donnell et al., J. Natl. Comp. Canc. Netw., Mar. 1, 2011, 9(3), p. 280-317.*

(Continued)

*Primary Examiner* — Jonathan S Lau
(74) *Attorney, Agent, or Firm* — Nelson Mullins Riley & Scarborough LLP; Cynthia L. Kanik (57) ABSTRACT

A first aspect of the invention relates to a method of treating AML in a subject, said method comprising administering to a subject a therapeutically effective amount of (i) sapacitabine, or a metabolite thereof; and (ii) decitabine; in accordance with a dosing regimen comprising at least one first treatment cycle and at least one second treatment cycle, wherein said first treatment cycle comprises administering a therapeutically effective amount of decitabine for 5 to 10 consecutive days followed by a rest period of from 3 to 5 weeks, or until treatment-related toxicities are resolved, whichever is longer; and wherein said second treatment cycle comprises administering a therapeutically effective amount of sapacitabine, or a metabolite thereof, for 3 consecutive days per week, for 2 weeks followed by a rest period of from 2 to 4 weeks, or until treatment-related toxicities are resolved, whichever is longer.

21 Claims, 3 Drawing Sheets

(56) References Cited

OTHER PUBLICATIONS

Johnson et al., J. Inherit. Metab. Dis., 2002, 25, p. 197-206. (Year: 2002).*
Anderson, A. GenomeWeb article, "Looking for Clues to Longevity, Disease Resistance in Super-Centenarian Genome", dated Oct. 25, 2011, https://www.genomeweb.com, accessed online on Jan. 22, 2018. (Year: 2011).*
International Preliminary Report on Patentability for Application No. PCT/GB2012/050815, 8 pages, dated Oct. 15, 2013.
Baer, Maria R. et al., "Novel Agents for the Treatment of Acute Myeloid Leukemia in the Older Patient," JNCCN, Journal of the National Comprehensive Cancer Network, vol. 9(3):331-335 (2011).
Kantarjian, Hagop et al., "Phase I Clinical and Pharmacokinetic Study of Oral Sapacitabine in Patients With Active Leukemia and Myelodysplastic Syndrome," Journal of Clinical Oncology, vol. 28(2):285-291 (2009).
Ravandi, F. et al., "Phase I/II study of sapacitabine and decitabine administered sequentially in elderly patient with newly diagnosed acute myeloid leukemia," Journal of Clinical Oncology, ASCO Annual Meeting Proceedings, vol. 29 (15 Suppl.) 1 page, Poster Presentation No. 6587 (2011).
International Search Report and Written Opinion for Application No. PCT/GB2012/050815, 13 pages, dated Aug. 16, 2012.
Accession No. 2000-565332, Hanaoka, K. et al., "Antitumor liposome preparations comprise sterol compound, phosphatidylcholine compound and 1-(2'-cyano-2'-deoxy-beta-arabino-pentofuranosyl) cytosine," (2000).
Accession No. 2001-040935, Hanaoka, K. et al., "Liposome preparation with high drug transfer contains 1-(2-C-cyano-2-deoxy-beta-D-arabinopentofuranosyl)-N4-palmitoyl cytosine antitumor agent," (2001).
Bellone, Graziella et al., "Antagonistic Interactions Between Gemcitabine and 5-Fluorouracil in the Human Pancreatic Carcinoma Cell Line Capan-2," Cancer Biology & Therapy, vol. 5(10):1294-1303 (2006).
Berge, Stephen M. et al., "Pharmaceutical Salts," Journal of Pharmaceutical Sciences, vol. 66(1):1-19 (1977).
Bible, Keith C. et al., "Cytotoxic Synergy between Flavopiridol (NSC 649890, L86-8275) and Various Antineoplastic Agents: The Importance of Sequence of Administration," Cancer Research, vol. 57:3375-3380 (1997).
Burch, P.A. et al., "Phase I Study of Orally Administered CS-682 in Solid Tumors," Proceedings of ASCO, vol. 20:92a, Poster No. 364 (2001).
CAplus, Accession No. 136:310184, Chong, Lee et al., "Preparation of hydroxamic acid peptide deformylase inhibitors as antibacterial agents," (2011).
Cashen A. F. et al., "Multicenter, phase II study of decitabine for the first-line treatment of older patients with acute myeloid leukemia," Journal of Clinical Oncology, vol. 28 (4):556-561 (2010).
Chou, Ting-Chao et al., "Quantitative Analysis of Dose-effect Relationships: The Combined Effects of Multiple Drugs or Enzyme Inhibitors," Adv. Enzyme Regul., vol. 22:27-55 (1984).
Danesi, Romano et al., "Pharmacogenetic determinants of anticancer drug activity and toxicity," Trends in Pharmacological Science, vol. 22(8):420-426 (2001).
De Vos, Dick et al., "Decitabine: a historical review of the development of an epigenetic drug," Ann. Hematol., vol. 84:3-8 (2005).
Delaunoit, Thierry et al., "A phase I clinical and pharmacokinetic study of CS-682 administered orally in advanced malignant solid tumors," Investigational New Drugs, vol. 24:327-333 (2006).
Donehower, Ross et al., "A Phase I Study of CS-682, an Oral Antimetabolite, in Patients with Refractory Solid Tumors," 2000 ASCO Meeting, Proc. Am. Soc. Clin. Oncol., vol. 19, Abstract No. 764 (2000).
Fenaux, Pierre, "Inhibitors of DNA methylation: beyond myelodysplastic syndromes," Nature Clinical Practice Oncology, vol. 2:S36-S44 (2005).
Fujita, F. et al., "Antitumor activity of a novel nucleoside 1-(2-C-cyano-2-deoxy-beta-D-arabino-pentofuranosy)-N4-palmitoylcytosine (CS-682)," Proceedings of the American Association for Cancer Research, 88th Annual Meeting, vol. 38:101-102, Abstract No. 681 (1997).
Gilbert, Jill et al., "A Phase I study of the oral antimetabolite, CS-682, administered once daily 5 days per week in patients with refractory solid tumor malignancies," Invest. New Drugs, vol. 24:499-508 (2006).
Green, Simon R. et al., "Synergistic Interactions Between Sapacitabine (CYC682) and Inhibitors of Either Histone Deacetylase or Methyltransferase in Acute Myeloid Leukemia Cell Lines," 100th Annual Meeting of the American Association for CancerResearch, Abstract No. 4552, 1 page (2009).
Hanaoka, K. et al., "A novel mechanism of action of a new antitumor nucleoside 1-(2-C-cyano-2-deoxy-beta-D-arabino-pentofuranosyl)-N4-Palmitoylcytosine (CS-682)," Proceedings of the American Association for Cancer Research, 88th Annual Meeting, vol. 38:101, Abstract No. 680 (1997).
Hanaoka, Kenji et al., "Antitumor Activity and Novel DNA-Self-Strand-Breaking Mechanism of CNDAC (1-(2-C-cyano-2-deoxy-b-D-arabino-pentofuranosyl) cytosine) and its N4-Palmitoyl Derivative (CS-682)," Int. J. Cancer, vol. 82:226-236 (1999).
Kaneko, M. et al., "Synthesis and antitumor activity of a novel antitumor nucleoside 1-(2-C-cyano-2-deoxy-beta-D-arabino-pentofuranosyl)-N4-palmitoylcytosine (CS-682)," Proceedings of the American Association for Cancer Research, 88th Annual Meeting, vol. 38:101, Abstract No. 679 (1997).
Kong, Xiang-Bin et al., "Induction of Deoxycytidine Kinase by 5-Azacytidine in an HL-60 Cell Line Resistant to Arabinosylcytosine," Molecular Pharmacology, vol. 39:250-257 (1991).
List, A. et al., "Developmental therapeutics for MDS," Leukemia Research, vol. 33:S27-S28 (2009).
Miyamoto, K. et al., "DNA methylation and cancer-DNA methylation as a target of cancer chemotherapy," Cancer and chemotherapy, vol. 30(13):2021-2029 (2003).
Peckham, Michael et al., "Biological and Pharmacological Basis of Chemotherapy, Biological Basis," Oxford Textbook of Oncology, vol. 1, Oxford University Press, Oxford, England, pp. 447-453 (1995).
Qin, Taichun et al., "Effect of Cytarabine and Decitabine in Combination in Human Leukemic Cell Lines," Clin Cancer Res., vol. 13(14):4225-4232 (2007).
Sankyo Co., Ltd., "CS-682," Drugs of the Future, vol. 24(9):957-960 (1999).
Serova, M. et al., "Antiproliferative effects of sapacitabine (CYC682), a novel 2'-deoxycytidine-derivative in human cancer cells," British Journal of Cancer, vol. 97:628-636 (2007).
Silverman, Richard B., "Drug Discovery, Design, and Development," The Organic Chemistry of Drug Design and Drug Action, Academic Press, San Diego, Chapter 2, pp. 4-47 (1992).
STN Database Descriptions, "Rapra," 2006 Chemical Abstracts Catalog, Chemical Abstracts Service, p. 52 (2006).
STN Gen Caesar Accession No. 1364, "Cyclacel's cancer drug starts Phase II testing," (2002).
Stresemann, Carlo et al., "Functional Diversity of DNA Methyltransferase Inhibitors in Human Cancer Cell Lines," Cancer Res., vol. 66(5):2794-2800 (2006).
The Merck Manual of Diagnosis and Therapy, Seventeenth Edition, Mark H. Beers (Ed.), Merck Research Laboratories, Whitehouse Station, N.J., pp. 397-398, 948-949, 1916 and 1979-1981 (1999).
Tolcher, A. et al., "Phase I study of sapacitabine, an oral nucleoside analogue, in patients with refractory solid tumors or lymphomas," European Journal of Cancer, Supplement, vol. 4(12):142, Poster No. 463 (2006).
Vippagunta, Sudha R. et al., "Crystalline solids," Advanced Drug Delivery Reviews, vol. 48:3-26 (2001).
Whittaker, Mark et al., "Design and Therapeutic Application of Matrix Metalloproteinase Inhibitors," Chem. Rev., vol. 99:2735-2776 (1999).
Whittaker, Mark et al., "MMP-12 inhibitors, AstraZeneca: WO2004020415," Expert Opin. Ther. Patents, vol. 14 (11):1637-1640 (2004).

(56) References Cited

OTHER PUBLICATIONS

Wu, Ming et al., "High-Resolution Magnetic Resonance Imaging of the Efficacy of the Cytosine Analogue 1-[2-C-Cyano-2-deoxy-b-D-arabino-pentofuranosyl]-N4-palmitoyl Cytosine (CS-682) in a Liver-Metastasis Athymic Nude Mouse Mode," Cancer Research,vol. 63:2477-2482 (2003).
Blum, W. et al., "Clinical response and miR-29b predictive significance in older AML patients treated with a 10-day schedule of decitabine," PNAS, vol. 107(16): 7473-7478 (2010).
Issa, J-P et al., "Phase 1 study of low-dose prolonged exposure schedules of the hypomethylating agent 5-aza-2'-deoxycytidine (decitabine) in hematopoietic malignancies," Blood, vol. 103 (5): 1635-1640 (2004).
Kantarjian, H. et al., "Multicenter, Randomized, Open-Label, Phase III Trial of Decitabine Versus Patient Choice, With Physician Advice, of Either Supportive Care or Low-Dose Cytarabine for the Treatment of Older Patients With Newly Diagnosed Acute Myeloid Leukemia," Journal of Clinical Oncology, vol. 30(21): 2670-2677 (2012).
Kantarjian, H. et al., "Oral sapacitabine for the treatment of acute myeloid leukaemia in elderly patients: a randomised phase 2 study," The Lancet.com/oncology, <http://dx.doi.org/10.1016/S1470-2045(12)70436-9>, 9 pages, (2012).
Ravandi, F. et al., "Pooled Analysis of Elderly Patients with Newly Diagnosed AML Treated with Sapacitabine and Decitabine Administered in Alternating Cycles," 54th ASH Annual Meeting and Exposition, Dec. 8-11, 2012, Abstract 2630 (2 pages).
European Medicines Agency: Guideline on Fixed Combination Medicinal Products, Doc. Ref. CPMP/EWP/240/95 Rev. 1, 7 pages (2008).
WHO: Annex 5, Guidelines for Registration of Fixed-dose Combination Medicinal Products, WHO Technical Report Series, No. 929: 94-142 (2005).
Dacogen® Prescribing Information Section 12, Table 3, Appendix A Oct. 2014.
Eleni, L. et al. "Challenges in Treating Older Patients with Acute Myeloid Leukemia," Journal of Oncology, Article ID 943823, vol. 2010, , 11 pages.
Erba, H. "Prognostic Factors in Elderly Patients with AML and the Implications for Treatment," American Society of Hematology, pp. 420-428 (2007).
Klepin, H. et al., "Acute Myelogenous Leukemia in Older Adults," The Oncologist, vol. 14:222-243 (2009).
Luger, S. "Treating the Elderly Patient with Acute Myelogenous Leukemia," Hematology, p. 62-69 (2010).
U.S. Appl. No. 10/581,585, filed Apr. 20, 2007, Simon Richard Green.
U.S. Appl. No. 12/093,427, filed Sep. 8, 2008, Simon Green.
U.S. Appl. No. 12/097,912, filed Sep. 19, 2008, Robert Westwood.
U.S. Appl. No. 12/517,196, filed Nov. 19, 2009, Simon Green.
U.S. Appl. No. 13/709,883, filed Dec. 10, 2012, Simon Green.
U.S. Appl. No. 12/597,293, filed Oct. 23, 2009, Judy Chiao.
U.S. Appl. No. 13/967,901, filed Aug. 15, 2013, Judy Chiao.
U.S. Appl. No. 12/265,553, filed Nov. 5, 2008, Athos Gianella-Borradori.
U.S. Appl. No. 12/991,582, filed Apr. 29, 2011, Gavin Wood.
U.S. Appl. No. 12/997,197, filed Apr. 5, 2011, Simon Richard Green.
U.S. Appl. No. 13/960,489, filed Aug. 6, 2013, Simon Richard Green.

* cited by examiner

DOSAGE REGIMEN FOR SAPACITABINE AND DECITABINE IN COMBINATION FOR TREATING ACUTE MYELOID LEUKEMIA

FIELD OF THE INVENTION

The present invention relates to a new dosing regimen suitable for the treatment of cancer and other proliferative disorders.

BACKGROUND TO THE INVENTION

DNA methyltransferases are a family of enzymes that promote the covalent addition of a methyl group to a specific nucleotide base in a molecule of DNA. All the known DNA methyltransferases use S-adenosyl methionine (SAM) as the methyl donor. Four active DNA methyltransferases have been identified in mammals. They are named DNMT1, DNMT2, DNMT3A and DNMT3B.

DNMT1 is the most abundant DNA methyltransferase in mammalian cells and considered to be the key maintenance methyltransferase in mammals. It predominantly methylates hemimethylated CpG di-nucleotides in the mammalian genome and is responsible for maintaining methylation patterns established in development. The enzyme is about 1620 amino acids long, the first 1100 amino acids constituting the regulatory domain, and the remaining residues constituting the catalytic domain. These are joined by Gly-Lys repeats. Both domains are required for the catalytic function of DNMT1. DNMT3 is a family of DNA methyltransferases that can methylate hemimethylated and unmethylated CpG at the same rate. The architecture of DNMT3 enzymes is similar to DNMT1 with a regulatory region attached to a catalytic domain.

Recent work has revealed how DNA methylation and chromatin structure are linked at the molecular level and how methylation anomalies play a direct causal role in tumorigenesis and genetic disease. Much new information has also come to light regarding DNA methyltransferases, in terms of their role in mammalian development and the types of proteins they are known to interact with. Rather than enzymes that act in isolation to copy methylation patterns after replication, the types of interactions discovered thus far indicate that DNA methyltransferases may be components of larger complexes actively involved in transcriptional control and chromatin structure modulation. These findings should enhance the understanding of the myriad roles of DNA methylation in disease, as well as leading to novel therapies for preventing or repairing these defects.

Small molecule DNA methyltransferase inhibitors are well documented in the art and include, for example, decitabine, azacitabine, zebularine, procainamide, procaine, hydralazine, ((−)-epigallocatechin-3-gallate (EGCG) and RG108.

Decitabine or 5-aza-2'-deoxycytidine (trade name Dacogen) is the compound 4-amino-1-(2-deoxy-b-D-erythro-pentofuranosyl)-1,3,5-triazin-2(1H)-one.

Azacitidine (trade name Vidaza) is the compound 4-amino-1-β-D-ribofuranosyl-s-triazin-2(1H)-one, the structure of which is shown below.

Azacitidine is an anti-neoplastic pyrimidine nucleoside analog used to treat several subtypes of myelodysplastic syndrome, diseases caused by abnormalities in the blood-forming cells of the bone marrow which result in underproduction of healthy blood cells. The drug exerts a cytotoxic effect on rapidly dividing cells, including cancerous cells, and may help restore normal function to genes controlling proper cellular differentiation and proliferation.

Azacitidine is specifically indicated for the treatment of the following myelodysplastic syndrome subtypes: refractory anemia, refractory anemia with ringed sideroblasts (if accompanied by neutropenia or thrombocytopenia or requiring transfusions), refractory anemia with excess blasts, refractory anemia with excess blasts in transformation and chronic myelomonocytic leukemia.

Azacitidine is believed to exert its antineoplastic effects by causing hypomethylation of DNA and direct cytotoxicity on abnormal haematopoietic cells in the bone marrow. The concentration of azacitidine required for maximum inhibition of DNA methylation in vitro does not cause major suppression of DNA synthesis. Hypomethylation may restore function to genes that are critical for differentiation or proliferation. The cytotoxic effects of azacitidine cause the death of rapidly dividing cells, including cancer cells that are no longer responsive to normal growth control mechanisms. Non-proliferating cells are relatively insensitive to azacitidine.

Another known DNA methyltransferase inhibitor is zebularine, also known as 1-(β-D-ribofuranosyl)-1,2-dihydropyrimidin-2-one or 2-pyrimidone-1-β-D-riboside, the structure of which is shown below.

Other known DNA methyltransferase inhibitors are non-nucleoside analogues, for example, procainamide, procaine, hydralazine and ((−)-epigallocatechin-3-gallate (EGCG).

Procainamide (trade names Pronestyl, Procan, Procanbid) is the compound 4-amino-N-(2-diethylaminoethyl)benzamide, the structure of which is shown below.

Procainamide has been shown to inhibit DNA methyltransferase activity and reactivate silenced gene expression in cancer cells by reversing CpG island hypermethylation. Procainamide specifically inhibits the hemimethylase activity of DNA methyltransferase 1 (DNMT1), the mammalian enzyme thought to be responsible for maintaining DNA methylation patterns during replication.

Procaine is the compound 2-(diethylamino)ethyl-4-aminobenzoate, the structure of which is shown below.

Procaine is a DNA-demethylating agent that is understood to inhibit DNA methyltransferases by interfering with enzyme activity.

Hydralazine (Apresoline) is the compound 1-hydrazinophthalazine monohydrochloride, the structure of which is shown below.

((−)-Epigallocatechin-3-gallate (EGCG) is a catechin analogue having the structure shown below.

EGCG is understood to inhibit DNMT activity and reactivate methylation-silenced genes in cancer cells.

Another known DNA methyltransferase inhibitor is RG108, also known as N-phthalyl-1-tryptophan, the structure of which is shown below.

RG108 is a DNA methyltransferase inhibitor that is understood to inhibit DNA methyltransferases by interfering with enzyme activity. In particular, RG108 is believed to reactivate tumor suppressor gene expression (p16, SFRP1, secreted frizzled related protein-1, and TIMP-3) in tumor cells by DNA demethylation. RG108 also inhibits human tumor cell line (HCT116, NALM-6) proliferation and increases doubling time in culture.

It is well established in the art that active pharmaceutical agents can often be given in combination in order to optimise the treatment regime.

Qin T et al (2007, 13, Clin. Cancer Res. 4225-4232) disclose the effect of combinations of cytarabine and decitabine in various human leukemic cell lines. Likewise, Kong X B et al (1991, Molecular Pharmacol. 39, 250-257) suggest that 5-azacitidine causes upregulation of dCK in a cell line that is resistant to cytarabine, resulting in a decrease in the $IC_{50}$ value for cytarabine from 12.5 to 0.55 μM.

Combinations of DNA methyltransferase inhibitors and 1-(2-C-cyano-2-dioxy-β-D-arabino-pentofuranosyl)-N4-palmitoyl cytosine (also known as "CYC682" or sapacitabine), or a metabolite thereof, are described in WO 2009/150405 (Cyclacel Limited). Pharmaceutical compositions comprising such combinations, and their use in treating various proliferative disorders are also described in WO 2009/150405.

The present invention seeks to provide a new dosing regimen for known pharmaceutical agents that is particularly suitable for the treatment of proliferative disorders, especially acute myeloid leukemia (AML). More specifically, the invention centres on the surprising and unexpected effects associated with using certain pharmaceutical agents in combination.

STATEMENT OF INVENTION

A first aspect of the invention relates to a method of treating AML in a subject, said method comprising administering to a subject a therapeutically effective amount of (i) sapacitabine, or a metabolite thereof; and (ii) decitabine; in accordance with a dosing regimen comprising at least one first treatment cycle and at least one second treatment cycle,
  wherein said first treatment cycle comprises administering a therapeutically effective amount of decitabine for 5 to 10 consecutive days followed by a rest period of from 3 to 5 weeks, or until treatment-related toxicities are resolved, whichever is longer; and
  wherein said second treatment cycle comprises administering a therapeutically effective amount of sapacitabine, or a metabolite thereof, for 3 consecutive days per week, for 2 weeks followed by a rest period of from 2 to 4 weeks, or until treatment-related toxicities are resolved, whichever is longer.

A second aspect of the invention relates to a method of treating AML in an elderly subject, said method comprising administering to a subject a therapeutically effective amount of (i) sapacitabine; and (ii) decitabine; in accordance with a dosing regimen comprising at least one first treatment cycle and at least one second treatment cycle,     wherein said first treatment cycle comprises administering decitabine intravenously in a dose of about 20 mg/m$^2$ for 5 to 10 consecutive days followed by a 3 to 5 week rest period, or until treatment-related toxicities are resolved, whichever is longer; and     wherein said second treatment cycle comprises administering sapacitabine orally in a dose of about 300 mg b.i.d. for 3 consecutive days per week, for 2 weeks followed by a 2 to 4 week rest period, or until treatment-related toxicities are resolved, whichever is longer.

A third aspect of the invention relates to (i) sapacitabine, or a metabolite thereof; and (ii) decitabine; for use in treating AML, wherein the sapacitabine, or a metabolite thereof, and the decitabine are administered in accordance with a dosing regimen comprising at least one first treatment cycle and at least one second treatment cycle,     wherein said first treatment cycle comprises administering a therapeutically effective amount of decitabine for 5 to 10 consecutive days followed by a rest period of from 3 to 5 weeks, or until treatment-related toxicities are resolved, whichever is longer; and     wherein said second treatment cycle comprises administering a therapeutically effective amount of sapacitabine, or a metabolite thereof, for 3 consecutive days per week, for 2 weeks followed by a rest period of from 2 to 4 weeks, or until treatment-related toxicities are resolved, whichever is longer.

A fourth aspect of the invention relates to (i) sapacitabine, or a metabolite thereof; and (ii) decitabine; for use in treating AML in an elderly subject, wherein the sapacitabine, or metabolite thereof, and decitabine, are administered in accordance with a dosing regimen comprising at least one first treatment cycle and at least one second treatment cycle,     wherein said first treatment cycle comprises administering decitabine intravenously in a dose of about 20 mg/m$^2$ per day for 5 to 10 consecutive days followed by a 3 to 5 week rest period, or until treatment-related toxicities are resolved, whichever is longer; and     wherein said second treatment cycle comprises administering sapacitabine orally in a dose of about 300 mg bid. for 3 consecutive days per week, for 2 weeks followed by a 2 to 4 week rest period, or until treatment-related toxicities are resolved, whichever is longer.

A fifth aspect of the invention relates to the use of (i) sapacitabine, or a metabolite thereof; and (ii) decitabine; in the preparation of a medicament for treating AML, wherein the sapacitabine, or a metabolite thereof, and the decitabine are administered in accordance with a dosing regimen comprising at least one first treatment cycle and at least one second treatment cycle,     wherein said first treatment cycle comprises administering a therapeutically effective amount of decitabine for 5 to 10 consecutive days followed by a rest period of from 3 to 5 weeks, or until treatment-related toxicities are resolved, whichever is longer; and     wherein said second treatment cycle comprises administering a therapeutically effective amount of sapacitabine, or a metabolite thereof, for 3 consecutive days per week, for 2 weeks followed by a rest period of from 2 to 4 weeks, or until treatment-related toxicities are resolved, whichever is longer.

A sixth aspect of the invention relates to the use of (i) sapacitabine, or a metabolite thereof; and (ii) decitabine; in the preparation of a medicament for treating AML in an elderly subject, wherein the sapacitabine, or metabolite thereof, and decitabine, are administered in accordance with a dosing regimen comprising at least one first treatment cycle and at least one second treatment cycle,     wherein said first treatment cycle comprises administering decitabine intravenously in a dose of about 20 mg/m$^2$ per day for 5 to 10 consecutive days followed by a 3 to 5 week rest period, or until treatment-related toxicities are resolved, whichever is longer; and     wherein said second treatment cycle comprises administering sapacitabine orally in a dose of about 300 mg b.i.d. for 3 consecutive days per week, for 2 weeks followed by a 2 to 4 week rest period, or until treatment-related toxicities are resolved, whichever is longer.

A seventh aspect of the invention relates to a kit of parts comprising:

(i) sapacitabine, or a metabolite thereof;

(ii) decitabine; and (iii) instructions for administering sapacitabine, or a metabolite thereof, and decitabine in accordance with a dosing regimen comprising at least one first treatment cycle and at least one second treatment cycle,     wherein said first treatment cycle comprises administering a therapeutically effective amount of decitabine for 5 to 10 consecutive days followed by a rest period of from 3 to 5 weeks, or until treatment-related toxicities are resolved, whichever is longer; and     wherein said second treatment cycle comprises administering a therapeutically effective amount of sapacitabine, or a metabolite thereof, for 3 consecutive days per week, for 2 weeks followed by a rest period of from 2 to 4 weeks, or until treatment-related toxicities are resolved, whichever is longer.

An eighth aspect of the invention relates to a kit of parts comprising:

(i) sapacitabine, or a metabolite thereof;

(ii) decitabine; and (iii) instructions for administering sapacitabine, or a metabolite thereof, and decitabine in accordance with a dosing regimen comprising at least one first treatment cycle and at least one second treatment cycle,     wherein said first treatment cycle comprises administering decitabine intravenously in a dose of about 20 mg/m$^2$ for 5 to 10 consecutive days followed by a 3 to 5 week rest period, or until treatment-related toxicities are resolved, whichever is longer; and     wherein said second treatment cycle comprises administering sapacitabine orally in a dose of about 300 mg b.i.d. for 3 consecutive days per week, for 2 weeks followed by a 2 to 4 week rest period, or until treatment-related toxicities are resolved, whichever is longer.

DETAILED DESCRIPTION

The effect of drug combinations is inherently unpredictable and there is often a propensity for one drug to partially or completely inhibit the effects of the other. The present invention is based on the surprising observation that administering 1-(2-C-cyano-2-dioxy-β-D-arabino-pentofuranosyl)-N4-palmitoyl cytosine and decitabine in accordance with a particular dosing regimen does not lead to any adverse interaction between the two agents. The unexpected absence of any such antagonistic interaction is critical for clinical applications.

In a preferred embodiment, the dosing regimen of the invention produces an enhanced effect as compared to either drug administered alone. The surprising nature of this observation is in contrast to that expected on the basis of the prior art.

Moreover, the presently claimed dosing regimen is well tolerated and gives rise to excellent response rates, good overall survival rates and absence of overlapping or cumulative toxicities.

1-(2-C-cyano-2-dioxy-β-D-arabino-pentofuranosyl)-N$^4$-palmitoyl cytosine (I), also known as 2'-cyano-2-deoxy-N$^4$-palmiotoyl-1-β-D-arabinofuranosylcytosine (Hanaoka, K., et al, *Int. J. Cancer,* 1999:82:226-236; Donehower R, et al, *Proc Am Soc Clin Oncol,* 2000: abstract 764; Burch, P A, et al, *Proc Am Soc Clin Oncol,* 2001: abstract 364), is an orally administered novel 2'-deoxycytidine antimetabolite prodrug of the nucleoside CNDAC, 1-(2-C-Cyano-2-deoxy-β-D-arabino-pentafuranosyl)-cytosine.

CNDAC 1-(2-C-cyano-2-dioxy-β-D-arabino-pentofuranosyl)-N$^4$-palmitoyl cytosine (I) (also known as "CYC682" or sapacitabine) has a unique mode of action over other nucleoside metabolites such as gemcitabine in that it has a spontaneous DNA strand breaking action, resulting in potent anti-tumour activity in a variety of cell lines, xenograft and metastatic cancer model.

1-(2-C-cyano-2-dioxy-β-D-arabino-pentofuranosyl)-N$^4$-palmitoyl cytosine (I) has been the focus of a number of studies in view of its oral bioavailability and its improved activity over gemcitabine (the leading marketed nucleoside analogue) and 5-FU (a widely-used antimetabolite drug) based on preclinical data in solid tumours. Recently, investigators reported that (I) exhibited strong anticancer activity in a model of colon cancer. In the same model, (I) was found to be superior to either gemcitabine or 5-FU in terms of increasing survival and also preventing the spread of colon cancer metastases to the liver (Wu M, et al, *Cancer Research,* 2003:63:2477-2482). To date, phase I data from patients with a variety of cancers suggest that (I) is well tolerated in humans, with myelosuppression as the dose limiting toxicity.

The DNA methyltransferase inhibitor used in the dosing regimen of the present invention is decitabine. Decitabine or 5-aza-2'-deoxycytidine (trade name Dacogen) is the compound 4-amino-1-(2-deoxy-b-D-erythro-pentofuranosyl)-1,3,5-triazin-2(1H)-one, the structure of which is shown below.

Decitabine is indicated for the treatment of myelodysplastic syndromes (MDS) including previously treated and untreated, de novo and secondary MDS of all French-American-British subtypes (refractory anemia, refractory anemia with ringed sideroblasts, refractory anemia with excess blasts, refractory anemia with excess blasts in transformation, and chronic myelomonocytic leukemia) and Intermediate-1, Intermediate-2, and High-Risk International Prognostic Scoring System groups.

Decitabine is believed to exert its antineoplastic effects after phosphorylation and direct incorporation into DNA. Decitabine inhibits DNA methyltransferase, causing hypomethylation of DNA and cellular differentiation or apoptosis. Decitabine-induced hypomethylation in neoplastic cells may restore normal function to genes that are critical for the control of cellular differentiation and proliferation. In rapidly dividing cells, the cytotoxicity of decitabine may also be attributed to the formation of covalent adducts between DNA methyltransferase and compound that has been incorporated into DNA. Non-proliferating cells are relatively insensitive to decitabine.

As used herein the phrase "preparation of a medicament" includes the use of the components of the invention directly as the medicament in addition to their use in any stage of the preparation of such a medicament.

In one preferred embodiment, the decitabine and 1-(2-C-cyano-2-dioxy-β-D-arabino-pentofuranosyl)-N4-palmitoyl cytosine are each administered in a therapeutically effective amount with respect to the individual components; in other words, the decitabine and 1-(2-C-cyano-2-dioxy-β-D-arabino-pentofuranosyl)-N4-palmitoyl cytosine are administered in amounts that would be therapeutically effective even if the components were administered other than in combination.

In another preferred embodiment, the decitabine and 1-(2-C-cyano-2-dioxy-β-D-arabino-pentofuranosyl)-N4-palmitoyl cytosine are each administered in a sub-therapeutic amount with respect to the individual components; in other words, the decitabine and 1-(2-C-cyano-2-dioxy-β-D-arabino-pentofuranosyl)-N4-palmitoyl cytosine are administered in amounts that would be therapeutically ineffective if the components were administered other than in combination.

Preferably, the 1-(2-C-cyano-2-dioxy-β-D-arabino-pentofuranosyl)-N4-palmitoyl cytosine and decitabine interact in a synergistic manner. As used herein, the term "synergistic" means that 1-(2-C-cyano-2-dioxy-β-D-arabino-pentofuranosyl)-N4-palmitoyl cytosine and the decitabine produce a greater effect when used in combination than would be expected from adding the individual effects of the two components. Advantageously, a synergistic interaction may allow for lower doses of each component to be administered to a patient, thereby decreasing the toxicity of chemotherapy, whilst producing and/or maintaining the same therapeutic effect. Thus, in a particularly preferred embodiment, each component can be administered in a sub-therapeutic amount.

Specific Dosing Regimens for Aml

Previous studies by the applicant have shown that in AML cell lines, the active metabolite of sapacitabine, CNDAC, is synergistic with hypomethylating agents and the synergy is more apparent if cells are treated with hypomethylating agents first.

One aspect of the invention therefore relates to a method of treating AML in a subject, said method comprising administering to a subject a therapeutically effective amount of (i) sapacitabine, or a metabolite thereof; and (ii) decitabine; in accordance with a dosing regimen comprising at least one first treatment cycle and at least one second treatment cycle, wherein said first treatment cycle comprises administering a therapeutically effective amount of decitabine for 5 to 10 consecutive days followed by a rest period of from 3 to 5 weeks, or until treatment-related toxicities are resolved, whichever is longer; and wherein said second treatment cycle comprises administering a therapeutically effective amount of sapacitabine, or a metabolite thereof, for 3 consecutive days per week, for 2 weeks followed by a rest period of from 2 to 4 weeks, or until treatment-related toxicities are resolved, whichever is longer.

The preferred embodiments set forth below apply equally to all aspects of the invention.

In one preferred embodiment, the second treatment cycle comprises administering a therapeutically effective amount of sapacitabine.

The sequential administration of decitabine and sapacitabine in alternating cycles in accordance with the presently claimed dosing regimen maximizes the efficacy of both drugs and minimizes overlapping myelosuppression.

The first and second treatment cycles are repeated sequentially with rest periods between sequential cycles, i.e. there is a rest period between the last day of decitabine administration and the first day of the second treatment cycle; likewise there is a rest period between the last day of sapacitabine administration and the first day of the next (first) treatment cycle. Preferably, the rest period is sufficient so as to resolve any treatment-related toxicities.

As used herein, treatment-related toxicities are mostly myelosuppression and its associated complications.

In one preferred embodiment, the first treatment cycle comprises administering a therapeutically effective amount of decitabine for 5 consecutive days followed by a rest period of from 3 to 5 weeks, or until treatment-related toxicities are resolved, whichever is longer.

In one preferred embodiment, the first treatment cycle comprises administering a therapeutically effective amount of decitabine for 5 days followed by a rest period of 3 to 5 weeks.

In a more preferred embodiment, the first treatment cycle comprises administering a therapeutically effective amount of decitabine for 5 days followed by a rest period of 3 weeks.

In one preferred embodiment, the first treatment cycle comprises administering a therapeutically effective amount of decitabine for 10 consecutive days followed by a rest period of from 3 to 5 weeks, or until treatment-related toxicities are resolved, whichever is longer.

In another preferred embodiment, the first treatment cycle comprises administering a therapeutically effective amount of decitabine for 10 days followed by a rest period of 4 weeks.

In one preferred embodiment, the second treatment cycle comprises administering a therapeutically effective amount of sapacitabine or metabolite thereof for 3 consecutive days per week, for 2 weeks, followed by a rest period of 2 to 4 weeks.

In a more preferred embodiment, the second treatment cycle comprises administering a therapeutically effective amount of sapacitabine or metabolite thereof for 3 consecutive days per week, for 2 weeks, followed by a rest period of 2 weeks.

In one preferred embodiment, the method comprises two or more of each treatment cycle, more preferably, three or more, four or more, or five or more of each treatment cycle.

In one highly preferred embodiment, the method comprises four or more of each treatment cycle.

In one highly preferred embodiment, the method comprises two to four of each treatment cycle.

In one preferred embodiment, the decitabine is administered intravenously.

In one preferred embodiment, the decitabine is administered in a dose of from about 10 to 20 mg/m$^2$ per day.

In a more preferred embodiment, the decitabine is administered in a dose of about 20 mg/m$^2$ per day. In certain preferred embodiments, the decitabine dosage may be tailored to individual patients within the same schedule in order to mitigate side effects. For example, in certain preferred embodiments the decitabine dosage may be reduced (typically in 5 mg/m$^2$ increments) from a starting dose of about 20 mg/m$^2$ per day, to about 15 mg/m$^2$ per day, or to about 10 mg/m$^2$ per day.

In one preferred embodiment, the decitabine is administered over a period of up to 3 hours per day, more preferably over a period of up to 2 hours per day, even more preferably over a period of about 1 hour per day.

In one preferred embodiment, the first treatment cycle comprises administering a therapeutically effective amount of decitabine in a dosage of about 20 mg/m$^2$ for 10 days, followed by a rest period of 4 weeks.

In one preferred embodiment, the sapacitabine or metabolite thereof is administered orally.

In one preferred embodiment, the sapacitabine or metabolite thereof is administered in a dose of about 100-400 mg b.i.d., more preferably from about 250-300 mg bid.

In a more preferred embodiment, the sapacitabine or metabolite thereof is administered in a dose of about 300 mg bid. In certain preferred embodiments, the sapacitabine dosage may be tailored to individual patients within the same schedule in order to mitigate side effects. For example, in certain preferred embodiments the sapacitabine dosage may be reduced (typically in 50 mg increments) from a starting dose of about 300 mg b.i.d. to about 250 mg b.i.d., or to about 200 mg b.i.d., or to about 150 mg b.i.d., or to about 100 mg b.i.d.

In one preferred embodiment, the subject is an elderly subject. As used herein, the term "elderly subject" refers to a subject of 60 years of age or over. More preferably, the subject is 65 years of age or over, even more preferably, 70 years of age or over, more preferably still, 75 years of age or over.

A further aspect of the invention relates to a method of treating AML in an elderly subject, said method comprising administering to a subject a therapeutically effective amount of (i) sapacitabine; and (ii) decitabine; in accordance with a dosing regimen comprising at least one first treatment cycle and at least one second treatment cycle,
   wherein said first treatment cycle comprises administering decitabine intravenously in a dose of about 20 mg/m$^2$ per day for 5 consecutive days followed by a 3 to 5 week rest period, or until treatment-related toxicities are resolved, whichever is longer; and
   wherein said second treatment cycle comprises administering sapacitabine orally in a dose of about 300 mg b.i.d. for 3 consecutive days per week, for 2 weeks followed by a 2 to 4 week rest period, or until treatment-related toxicities are resolved, whichever is longer.

In one highly preferred embodiment, the dosing regimen comprises administering decitabine at 20 mg/m$^2$ per day for 5 consecutive days of a 4-week cycle (odd cycles) and sequentially sapacitabine at 300 mg orally twice per day for three days per week for two weeks of a 4-week cycle (even cycles).

A further aspect of the invention relates to a method of treating AML in an elderly subject, said method comprising administering to a subject a therapeutically effective amount of (i) sapacitabine; and (ii) decitabine; in accordance with a dosing regimen comprising at least one first treatment cycle and at least one second treatment cycle,
   wherein said first treatment cycle comprises administering decitabine intravenously in a dose of about 20 mg/m$^2$ per day for 10 consecutive days followed by a 3 to 5 week rest period, or until treatment-related toxicities are resolved, whichever is longer; and
   wherein said second treatment cycle comprises administering sapacitabine orally in a dose of about 300 mg b.i.d. for 3 consecutive days per week, for 2 weeks followed by a 2 to 4 week rest period, or until treatment-related toxicities are resolved, whichever is longer.

In one highly preferred embodiment, the dosing regimen comprises administering decitabine at 20 mg/m$^2$ per day for 10 consecutive days of a 4-week cycle (odd cycles) and sequentially sapacitabine at 300 mg orally twice per day for three days per week for two weeks of a 4-week cycle (even cycles).

A further aspect of the invention relates to (i) sapacitabine, or a metabolite thereof; and (ii) decitabine; for use in treating AML, wherein the sapacitabine, or metabolite thereof, and the decitabine are administered in accordance with a dosing regimen comprising at least one first treatment cycle and at least one second treatment cycle,
   wherein said first treatment cycle comprises administering a therapeutically effective amount of decitabine for 5 or 10 consecutive days followed by a rest period of from 3 to 5 weeks, or until treatment-related toxicities are resolved, whichever is longer; and
   wherein said second treatment cycle comprises administering a therapeutically effective amount of sapacitabine, or a metabolite thereof, for 3 consecutive days per week, for 2 weeks followed by a rest period of from 2 to 4 weeks, or until treatment-related toxicities are resolved, whichever is longer.

Another aspect of the invention relates to (i) sapacitabine, or a metabolite thereof; and (ii) decitabine; for use in treating AML in an elderly subject, wherein the sapacitabine, or metabolite thereof, and decitabine, are administered in accordance with a dosing regimen comprising at least one first treatment cycle and at least one second treatment cycle,
   wherein said first treatment cycle comprises administering decitabine intravenously in a dose of about 20 mg/m$^2$ per day for 5 or 10 consecutive days followed by a 3 to 5 week rest period, or until treatment-related toxicities are resolved, whichever is longer; and
   wherein said second treatment cycle comprises administering sapacitabine orally in a dose of about 300 mg for 3 consecutive days per week, for 2 weeks followed by a 2 to 4 week rest period, or until treatment-related toxicities are resolved, whichever is longer.

A further aspect of the invention relates to the use of (i) sapacitabine, or a metabolite thereof; and (ii) decitabine; in the preparation of a medicament for treating AML, wherein the sapacitabine, or metabolite thereof, and the decitabine are administered in accordance with a dosing regimen comprising at least one first treatment cycle and at least one second treatment cycle,
   wherein said first treatment cycle comprises administering a therapeutically effective amount of decitabine for 5 or 10 consecutive days followed by a rest period of from 3 to 5 weeks, or until treatment-related toxicities are resolved, whichever is longer; and
   wherein said second treatment cycle comprises administering a therapeutically effective amount of sapacitabine, or a metabolite thereof, for 3 consecutive days per week, for 2 weeks followed by a rest period of from 2 to 4 weeks, or until treatment-related toxicities are resolved, whichever is longer.

Another aspect of the invention relates to the use of (i) sapacitabine, or a metabolite thereof; and (ii) decitabine; in the preparation of a medicament for treating AML in an elderly subject, wherein the sapacitabine, or metabolite thereof, and decitabine are administered in accordance with a dosing regimen comprising at least one first treatment cycle and at least one second treatment cycle,
   wherein said first treatment cycle comprises administering decitabine intravenously in a dose of about 20 mg/m$^2$ per day for 5 or 10 consecutive days followed by a 3 to 5 week rest period, or until treatment-related toxicities are resolved, whichever is longer; and
   wherein said second treatment cycle comprises administering sapacitabine orally in a dose of about 300 mg b.i.d. for 3 consecutive days per week, for 2 weeks followed by a 2 to 4 week rest period, or until treatment-related toxicities are resolved, whichever is longer.

Kit of Parts

A further aspect of the invention relates to a kit of parts comprising:
(i) sapacitabine, or a metabolite thereof;
(ii) decitabine; and
(iii) instructions for administering sapacitabine, or a metabolite thereof, and decitabine in accordance with a dosing regimen comprising at least one first treatment cycle and at least one second treatment cycle, wherein said first treatment cycle comprises administering a therapeutically effective amount of decitabine for 5 to 10 consecutive days followed by a rest period of from 3 to 5 weeks, or until treatment-related toxicities are resolved, whichever is longer; and wherein said second treatment cycle comprises administering a therapeutically effective amount of sapacitabine, or a metabolite thereof, for 3 consecutive days per week, for 2 weeks followed by a rest period of from 2 to 4 weeks, or until treatment-related toxicities are resolved, whichever is longer.

Another aspect of the invention relates to a kit of parts comprising:
(i) sapacitabine, or a metabolite thereof;
(ii) decitabine; and
(iii) instructions for administering sapacitabine, or a metabolite thereof, and decitabine in accordance with a dosing regimen comprising at least one first treatment cycle and at least one second treatment cycle, wherein said first treatment cycle comprises administering decitabine intravenously in a dose of about 20 mg/m$^2$ for 5 to 10 consecutive days followed by a 3 to 5 week rest period, or until treatment-related toxicities are resolved, whichever is longer; and wherein said second treatment cycle comprises administering sapacitabine orally in a dose of about 300 mg b.i.d. for 3 consecutive days per week, for 2 weeks followed by a 2 to 4 week rest period, or until treatment-related toxicities are resolved, whichever is longer.

Preferably, the kit of parts is for use in treating ALM in a subject, preferably an elderly subject.

Metabolite

As used herein, the term "metabolite" encompasses chemically modified entities that are produced by metabolism of 1-(2-C-cyano-2-dioxy-β-D-arabino-pentofuranosyl)-N4-palmitoyl cytosine.

In one particularly preferred embodiment of the invention, the metabolite of 1-(2-C-cyano-2-dioxy-β-D-arabino-pentofuranosyl)-N4-palmitoyl cytosine is 2'-C'-cyano-2'-dioxy-1-β-D-arabino-pentofuranosyl cytosine (CNDAC).

In another particularly preferred embodiment of the invention, 1-(2-C-cyano-2-dioxy-β-D-arabino-pentofuranosyl)-N4-palmitoyl cytosine is metabolized intracellularly to the active metabolite CNDAC-triphosphate (CNDACTP), a process involving both the cleavage of the palmitoyl moiety and activation to CNDACTP by the action of nucleoside kinases.

Salts/Esters

The agents of the present invention can be present as salts or esters, in particular pharmaceutically acceptable salts or esters.

Pharmaceutically acceptable salts of the agents of the invention include suitable acid addition or base salts thereof. A review of suitable pharmaceutical salts may be found in Berge et al, J Pharm Sci, 66, 1-19 (1977). Salts are formed, for example with strong inorganic acids such as mineral acids, e.g. sulphuric acid, phosphoric acid or hydrohalic acids; with strong organic carboxylic acids, such as alkanecarboxylic acids of 1 to 4 carbon atoms which are unsubstituted or substituted (e.g., by halogen), such as acetic acid; with saturated or unsaturated dicarboxylic acids, for example oxalic, malonic, succinic, maleic, fumaric, phthalic or tetraphthalic; with hydroxycarboxylic acids, for example ascorbic, glycolic, lactic, malic, tartaric or citric acid; with aminoacids, for example aspartic or glutamic acid; with benzoic acid; or with organic sulfonic acids, such as ($C_1$-$C_4$)-alkyl- or aryl-sulfonic acids which are unsubstituted or substituted (for example, by a halogen) such as methane- or p-toluene sulfonic acid.

Esters are formed either using organic acids or alcohols/hydroxides, depending on the functional group being esterified. Organic acids include carboxylic acids, such as alkanecarboxylic acids of 1 to 12 carbon atoms which are unsubstituted or substituted (e.g., by halogen), such as acetic acid; with saturated or unsaturated dicarboxylic acid, for example oxalic, malonic, succinic, maleic, fumaric, phthalic or tetraphthalic; with hydroxycarboxylic acids, for example ascorbic, glycolic, lactic, malic, tartaric or citric acid; with aminoacids, for example aspartic or glutamic acid; with benzoic acid; or with organic sulfonic acids, such as ($C_1$-$C_4$)-alkyl- or aryl-sulfonic acids which are unsubstituted or substituted (for example, by a halogen) such as methane- or p-toluene sulfonic acid. Suitable hydroxides include inorganic hydroxides, such as sodium hydroxide, potassium hydroxide, calcium hydroxide, aluminium hydroxide. Alcohols include alkanealcohols of 1-12 carbon atoms which may be unsubstituted or substituted, e.g. by a halogen).

Enantiomers/Tautomers

The invention also includes where appropriate all enantiomers and tautomers of the agents. The man skilled in the art will recognise compounds that possess an optical properties (one or more chiral carbon atoms) or tautomeric characteristics. The corresponding enantiomers and/or tautomers may be isolated/prepared by methods known in the art.

Stereo and Geometric Isomers

Some of the agents of the invention may exist as stereoisomers and/or geometric isomers—e.g. they may possess one or more asymmetric and/or geometric centres and so may exist in two or more stereoisomeric and/or geometric forms. The present invention contemplates the use of all the individual stereoisomers and geometric isomers of those inhibitor agents, and mixtures thereof. The terms used in the claims encompass these forms, provided said forms retain the appropriate functional activity (though not necessarily to the same degree).

The present invention also includes all suitable isotopic variations of the agent or pharmaceutically acceptable salts thereof. An isotopic variation of an agent of the present invention or a pharmaceutically acceptable salt thereof is defined as one in which at least one atom is replaced by an atom having the same atomic number but an atomic mass different from the atomic mass usually found in nature. Examples of isotopes that can be incorporated into the agent and pharmaceutically acceptable salts thereof include isotopes of hydrogen, carbon, nitrogen, oxygen, phosphorus, sulphur, fluorine and chlorine such as $^2$H, $^3$H, $^{13}$C, $^{14}$C, $^{15}$N, $^{17}$O, $^{18}$O, $^{31}$P, $^{32}$P, $^{35}$S, $^{18}$F and $^{36}$Cl, respectively. Certain isotopic variations of the agent and pharmaceutically acceptable salts thereof, for example, those in which a radioactive isotope such as $^3$H or $^{14}$C is incorporated, are useful in drug and/or substrate tissue distribution studies. Tritiated, i.e., $^3$H, and carbon-14, i.e., $^{14}$C, isotopes are particularly preferred for their ease of preparation and detectability. Further, substitution with isotopes such as deuterium, i.e., $^2$H, may afford certain therapeutic advantages resulting from greater metabolic stability, for example, increased in vivo half-life or reduced dosage requirements and hence may be preferred in some circumstances. Isotopic variations of the agent of the present invention and pharmaceutically acceptable salts thereof of this invention can generally be prepared by conventional procedures using appropriate isotopic variations of suitable reagents.

Solvates

The present invention also includes solvate forms of the agents of the present invention. The terms used in the claims encompass these forms.

Polymorphs

The invention furthermore relates to agents of the present invention in their various crystalline forms, polymorphic forms and (an)hydrous forms. It is well established within the pharmaceutical industry that chemical compounds may be isolated in any of such forms by slightly varying the method of purification and or isolation form the solvents used in the synthetic preparation of such compounds.

Prodrugs

The invention further includes agents of the present invention in prodrug form. Such prodrugs are generally compounds wherein one or more appropriate groups have been modified such that the modification may be reversed upon administration to a human or mammalian subject. Such reversion is usually performed by an enzyme naturally present in such subject, though it is possible for a second agent to be administered together with such a prodrug in order to perform the reversion in vivo. Examples of such modifications include ester (for example, any of those described above), wherein the reversion may be carried out be an esterase etc. Other such systems will be well known to those skilled in the art.

Administration

The pharmaceutical compositions of the present invention may be adapted for oral, rectal, vaginal, parenteral, intramuscular, intraperitoneal, intraarterial, intrathecal, intrabronchial, subcutaneous, intradermal, intravenous, nasal, buccal or sublingual routes of administration.

For oral administration, particular use is made of compressed tablets, pills, tablets, gellules, drops, and capsules. Preferably, these compositions contain from 1 to 2000 mg and more preferably from 50-1000 mg, of active ingredient per dose.

Other forms of administration comprise solutions or emulsions which may be injected intravenously, intraarterially, intrathecally, subcutaneously, intradermally, intraperitoneally or intramuscularly, and which are prepared from sterile or sterilisable solutions. The pharmaceutical compositions of the present invention may also be in form of suppositories, pessaries, suspensions, emulsions, lotions, ointments, creams, gels, sprays, solutions or dusting powders.

An alternative means of transdermal administration is by use of a skin patch. For example, the active ingredient can be incorporated into a cream consisting of an aqueous emulsion of polyethylene glycols or liquid paraffin. The active ingredient can also be incorporated, at a concentration of between 1 and 10% by weight, into an ointment consisting of a white wax or white soft paraffin base together with such stabilisers and preservatives as may be required.

Injectable forms may contain between 10-1000 mg, preferably between 10-500 mg, of active ingredient per dose.

Compositions may be formulated in unit dosage form, i.e., in the form of discrete portions containing a unit dose, or a multiple or sub-unit of a unit dose.

In a particularly preferred embodiment, the combination or pharmaceutical composition of the invention is administered intravenously.

Dosage

A person of ordinary skill in the art can easily determine an appropriate dose of one of the instant compositions to administer to a subject without undue experimentation. Typically, a physician will determine the actual dosage which will be most suitable for an individual patient and it will depend on a variety of factors including the activity of the specific compound employed, the metabolic stability and length of action of that compound, the age, body weight, general health, sex, diet, mode and time of administration, rate of excretion, drug combination, the severity of the particular condition, and the individual undergoing therapy. The dosages disclosed herein are exemplary of the average case. There can of course be individual instances where higher or lower dosage ranges are merited, and such are within the scope of this invention.

Depending upon the need, the agent may be administered at a dose of from 0.1 to 30 mg/kg body weight, such as from 2 to 20 mg/kg, more preferably from 0.1 to 1 mg/kg body weight.

By way of guidance, 1-(2-C-cyano-2-dioxy-β-D-arabino-pentofuranosyl)-N4-palmitoyl cytosine is typically administered in accordance with a physician's direction at total dosages of between 100 mg and 800 mg per day. Preferably, the dose is administered orally. The doses can be given 5 days a week for 4 weeks, or 3 days a week for 4 weeks. Dosages and frequency of application are typically adapted to the general medical condition of the patient and to the severity of the adverse effects caused, in particular to those caused to the hematopoietic, hepatic and to the renal system. The total daily dose can be administered as a single dose or divided into separate dosages administered two, three or four time a day.

The DNA methyltransferase inhibitor decitabine (Dacogen®) is typically administered subcutaneously or intravenously in accordance with a physician's direction. By way of guidance, the recommended decitabine dose is 15 mg/m$^2$ administered by continuous intravenous infusion over 3 h repeated every 8 h for 3 days (decitabine clinical label; Fenaux P. (2005) Nature Clinical Practice, 2, S36-44). This cycle is preferably repeated every 6 weeks. Patients with advanced solid tumours typically receive a 72 h infusion of decitabine at 20-30 mg/m$^2$/day.

Alternatively, decitabine may be administered at a dose of 20 mg/m$^2$ by continuous intravenous infusion over 1 hour repeated daily for 5 days. The cycle is repeated every 4 weeks (see FDA approved drug label for decitabine).

The present invention is further described by way of example, and with reference the following Figures, wherein:

FIG. 1 shows the effect of azacitidine in combination with CNDAC on the cell cycle profile and induction of apoptosis in HL60 cells after 72 hours. (A) HL60 cells were treated with 128 nM azacitidine for 24 hours followed by 128 nM azacitidine and 133 nM CNDAC for a further 48 hours. Cells were fixed and DNA stained with propidium iodide. Single agent controls were also included. (B) HL60 cells were treated with 128 nM azacitidine for 24 hours followed by 128 nM azacitidine and 133 nM CNDAC for a further 48 hours. Cells were stained with annexin V that detected apoptotic cells and propidium iodide to detect viable cells. Single agent controls were also included. Data is the average of two samples and representative of at least two independent experiments.

FIG. 2 shows the effect of azacitidine in combination with CNDAC on the cell cycle profile and induction of apoptosis in HL60 cells after 96 hours. (A) HL60 cells were treated with 128 nM azacitidine for 24 hours followed by 128 nM azacitidine and 133 nM CNDAC for a further 72 hours. Cells were fixed and DNA stained with propidium iodide. Single agent controls were also included. (B) HL60 cells were treated with 128 nM azacitidine for 24 hours followed by 128 nM azacitidine and 133 nM CNDAC for a further 72 hours. Cells were stained with annexin V that detected apoptotic cells and propidium iodide to detect viable cells. Single agent controls were also included. Data is the average of two samples and representative of at least two independent experiments.

EXAMPLES

Materials & Methods

Cell Lines and Reagents

MV4-11, HL60 and CEM cells were purchased from the ECACC (Salisbury, UK) ATCC. Cells were cultured at 37° C. with 5% CO2 in RPMI 1640 media containing 10% fetal calf serum (FCS). Cells were kept at a density of between $0.2 \times 10^6$ and $1 \times 10^6$ cells/ml.

CNDAC was prepared in accordance with the methodology set forth in EP 535231B (Sankyo Company Limited). CYC682 (sapacitabine) was prepared in accordance with the methodology described in EP 536936B (Sankyo Company Limited). Decacitabine and Azacitidine were purchased from Sigma-Aldrich. Stock solutions of all compounds were prepared in dimethyl sulphoxide (DMSO) at 10 mM. All reagents were purchased from Sigma (Poole, UK) unless stated otherwise.

Cell Culture/Cytotoxicity Assays

In order to complete the combination studies, the cytotoxic effects of individual compounds were determined. To establish the 72 hour $IC_{50}$ for each compound, experiments were carried out in 96-well plates and the cell lines seeded at a density of 5,000/well for MV4-11 and HL60 cells and 6,000/well for CCRF-CEM cells. In each cell line, 72 h treatment $IC_{50}$ values were determined for each compound using the alamar blue assay.

A dilution series for each drug was prepared in medium. Two hours after seeding, an equal volume of each compound was added at twice the desired concentration and incubated for 72 hours. All treatments were performed in triplicate. At the end of the incubation, a 20% stock of alamar blue (Roche, Lewes, UK) was prepared in media, and an equal volume was added to each well and incubated for three hours. Absorbance was read at 544-595 nm and data was analysed (Excel Fit v4.0) to determine the $IC_{50}$ (concentration of compound that inhibited cell growth by 50%) for each compound.

CNDAC was then tested in combination with decitabine or azacitidine using three different treatment regimes: concomitant, CNDAC pre-treatment followed by methyltransferase inhibitor, and methyltransferase inhibitor pretreatment followed by CNDAC.

Calcusyn Drug Combination Protocol

Combination treatments were evaluated as follows: a cytotoxicity assay was used treating cells with two drugs at a range of concentrations and analysed using the median effect model (Chou and Talalay, 1984). For the cytotoxicity assays, treatments were either concomitant (e.g. nucleoside analogue+DMTi) or 24 hours pre-treatment of nucleoside analogue followed by 72 hours with concomitant treatment of both agents (nucleoside analogue–DMTi) and vice versa (DMTi–nucleoside analogue). Purely sequential treatments were not possible to perform with suspension cell lines. The dosing used was based around the $IC_{50}$ for 72 hours.

Since MV4-11, HL60 and CCRF-CEM cells do not adhere to 96-well plates, it was not practical to aspirate the medium from the wells, so the pre-treatment compounds were not removed during the combination experiments. For the combination analysis, 2-fold serial dilutions of each compound were used, with the concentration range of the single agents chosen so that it spanned the $IC_{50}$ value of the compound. CNDAC, decitabine and azacitidine were dissolved in DMSO prior to adding compound to media.

For the concomitant treatment, serial dilutions of CNDAC, methyltransferase inhibitor, or both drugs simultaneously were added to cells 24 h after plating, and left for 72 h at 37° C.

In the pre-treatment regimes, the first drug was added immediately after cells were plated, and left for 24 h. Fresh medium containing the second drug was then added, and incubated for 72 h. The two controls for each sequential treatment involved substituting one of the drug treatments with medium. All treatments were performed in triplicate.

After drug treatment, the cell number in each well was then estimated by incubating the cells for approximately 6 h in medium containing 10% alamar blue (Roche, Lewes, East Sussex, U.K.) and reading the absorbance at 544-595 nm. Drug interactions were analysed using the commercial software package Calcusyn, which is based on the median effect model of Chou and Talalay (Chou, T. C. & Talalay, P. (1984) Adv. Enzyme Regul. 22, 27-55. Quantatative analysis of dose-effect relationships: the combined effects of multiple drugs or enzyme inhibitors). A Combination Index (C.A.) of 1 indicated an additive drug interaction, whereas a C.I. greater than 1 was antagonistic and a score lower than 1 was synergistic. The CI value definitions are as follows: 1.45-1.2 is moderately antagonistic, 1.2-1.1 is slightly antagonistic, 1.1-0.9 is additive, 0.9-0.85 is slightly synergistic, 0.85-0.7 is moderately synergistic and 0.7-0.3 is synergistic.

Cell Cycle Analysis

Cell treatments were as follows: for single agent evaluation, HL60 cells were seeded in triplicate at $0.3 \times 10^6$ cells/ml in medium and were treated with 128 nM (0.5× $IC_{50}$) azacitidine or 133 nM (1×$IC_{50}$) CNDAC or DMSO only for 48 or 72 hours before harvesting for flow cytometry. For combination analysis, cells were treated with azacitidine for 24 hours followed by a further 48 or 72 hours with azacitidine and CNDAC. For controls, single agent treatments for each drug were also performed. At the end of the incubation, cells were harvested by washing twice in PBS and fixation in 70% ethanol and storage at −20° C. Prior to analysis cells were washed twice in PBS containing 1% BSA followed by staining with propidium iodide (50 µg/ml) and ribonuclease A (50 µg/ml) in PBS containing 0.1% Triton X-100 and the cell cycle profile was determined by flow cytometry.

Annexin V Staining

HL60 cells were pre-treated with 128 nM azacitidine (equivalent to 0.5×$IC_{50}$) for 24 hours followed by concomitant treatment with 128 nM azacitidine and 133 nM CNDAC (equivalent to 1×$IC_{50}$) for 48 or 72 hours. Single agent treatments were also performed as controls. After incubation cells were centrifuged at 500 g for 5 min, washed twice in PBS and once in annexin buffer (10 mM Hepes pH 7.4, 2.5 mM CaCl2, and 140 mM NaCl). Cells were resuspended at $1 \times 10^6$/ml and 100 µl was transferred to a 5 ml tube prior to incubation for 10 min in the dark at room temperature with 5 µl of annexin V-FITC stain (Beckton Dickinson) and 10 µl of propidium iodide [50 mg/ml]. Annexin buffer (1 ml) was added and the cells were analysed by flow cytometry. Annexin V positive cells (apoptotic) were designated on the basis of green fluorescence and propidium iodide (dead) positive cells were designated on the basis of red fluorescence.

Preparation and Analysis of Cell Lysates by Immunoblotting

Cells were seeded at $0.3 \times 10^6$ cells/ml in T25 flasks and treated with either DMSO, or azacitidine at 128 nM (equivalent to $0.5 \times IC_{50}$) for 24 hours followed by concomitant treatment with 128 nM azacitidine and 133 nM CNDAC (equivalent to $1 \times IC_{50}$) for a further 24, 36, 40, 48 and 72 hours.

Cells were harvested by centrifugation at 500 g for 5 min, washed once with ice-cold PBS and resuspended in 100 µl of lysis buffer (50 mM HEPES, pH 7.0, 20 mM NaCl, 1 mM DTT, 1× protease inhibitors, 10 mM sodium pyrophosphate, 10 mM NaF and 1 mM $Na_3VO_4$). All samples were lysed by sonication (2×3s bursts using Sanyo soniprep 150 at 5 amp setting). The protein concentration of each lysate was determined using the BCA assay (Perbio Science, Northumberland, U.K.). Lysate (30 µg) was mixed with gel loading buffer containing reducing agent and separated on 10% or 12% polyacrylamide gels using denaturing electrophoretic conditions according to manufacturers instructions (Invitrogen, Glasgow, UK). Proteins were transferred to nitrocellulose membranes (Hybond ECL, Amersham, Chalfont St. Giles, UK) using wet electrophoretic transfer. Membranes were stained with ponceau S to confirm equal loading before blocking in 5% non-fat milk in PBS with 0.1% Tween 20 (PBSTM) for 1 hour. Membranes were incubated overnight at 4° C. with primary antibody, diluted in PBSTM. Antibodies used in this study were: cleaved PARP (Becton Dickinson). Membranes were washed in PBS and 0.1% Tween 20 (PBST) and incubated for 1 hour in PBSTM containing horseradish peroxidase-conjugated secondary antibody. Membranes were washed and incubated with ECL solution (Amersham) and exposed to X-ray film (Amersham).

Results

CNDAC and Decitabine in Combination in Haematological Cell Lines

CNDAC was tested in combination with decitabine in the AML cell lines HL60 and MV4-11, and the ALL cell line CCRF-CEM using three different treatment regimes. The Combination Index values from each drug treatment are shown for ED50, ED75 and ED90 values in Table 1 (the point on the curve where 50%, 75% and 90% of the cells have been killed). Data are the average of three independent experiments.

TABLE 1

| Cell Line | Effect | CNDAC pretreatment | Decitabine pretreatment | Concomitant |
|---|---|---|---|---|
| MV4-11 | ED50 | 0.95 | 1.17 | 0.79 |
| (n = 3) | ED75 | 0.71 | 0.66 | 0.88 |
|  | ED90 | 0.59 | 0.44 | 1.06 |
| HL60 | ED50 | 1.16 | 0.6 | 1.47 |
| (n = 3) | ED75 | 0.64 | 0.48 | 1.1 |
|  | ED90 | 0.68 | 0.62 | 1.86 |
| CCRF- | ED50 | 0.58 | 0.94 | 1.29 |
| CEM | ED75 | 0.5 | 0.68 | 0.85 |
| (n = 3) | ED90 | 0.64 | 0.52 | 0.85 |

CNDAC and decitabine generated moderate to strong synergy in all three cell lines tested. CNDAC pre-treatment and decitabine pretreatment were both particularly effective treatment regimes for this combination. These results support the idea of combining CNDAC with decitabine in haematological cell lines.

CNDAC and Azacitidine in Combination in Haematological Cell Lines

CNDAC was tested in combination with azacitidine in the AML cell lines HL60 and MV4-11, and the ALL cell line CCRF-CEM using three different treatment regimes. The Combination Index values from each drug treatment are shown for ED50, ED75 and ED90 values in Table 2 (the point on the curve where 50%, 75% and 90% of the cells have been killed). Data are the average of three independent experiments.

TABLE 2

| Cell Line | Effect | CNDAC pretreatment | Azacitidine pretreatment | Concomitant |
|---|---|---|---|---|
| MV4-11 | ED50 | 1.23 | 1.09 | 1.13 |
| (n = 3) | ED75 | 0.95 | 1.04 | 1.03 |
|  | ED90 | 0.77 | 1.02 | 0.96 |
| HL60 | ED50 | 1.33 | 0.91 | 1.24 |
| (n = 3) | ED75 | 1.13 | 0.6 | 1.11 |
|  | ED90 | 1.03 | 0.4 | 0.99 |
| CCRF- | ED50 | 0.75 | 0.76 | 1.02 |
| CEM | ED75 | 0.71 | 0.61 | 1.09 |
| (n = 3) | ED90 | 0.72 | 0.51 | 1.19 |

CNDAC and azacitidine induced moderate to strong synergy in all three cell lines tested. Azacitidine pretreatment generated strong synergy in HL60 and CEM cells, whereas CNDAC pre-treatment produced moderate synergy in MV4-11 and CEM cells. These results support the idea of combining CNDAC with azacitidine in haematological cell lines.

Cell Cycle Analysis

Figure 1A:
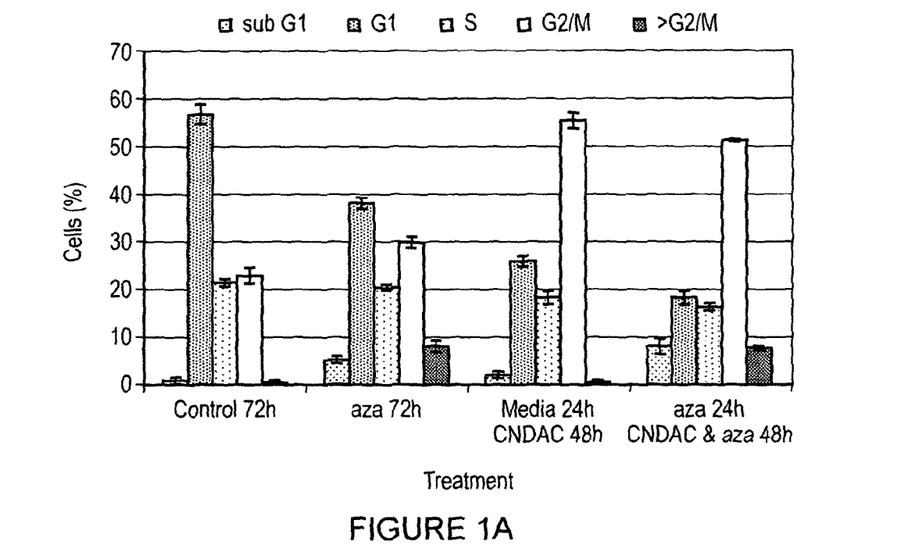
Figure 2A:
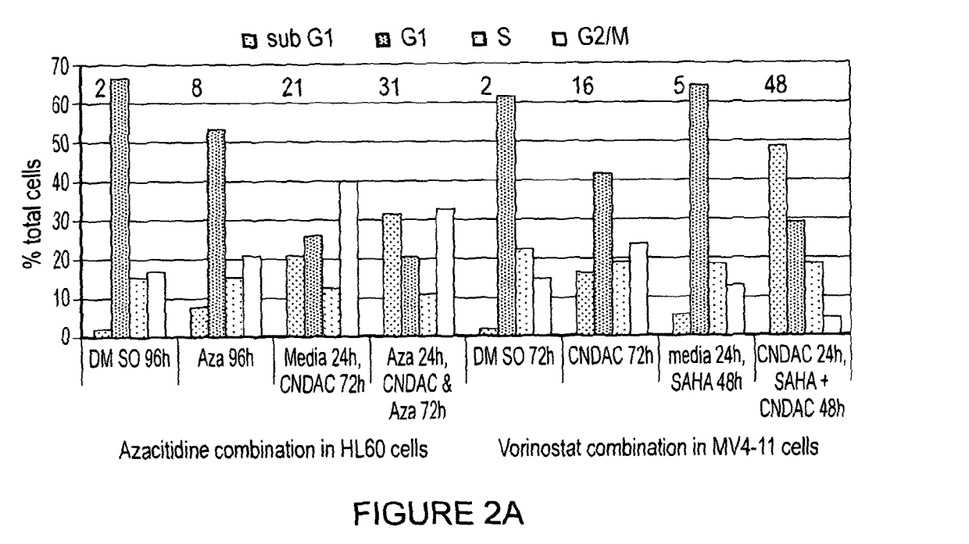

HL-60 or MV4-11 cells were treated with DMSO, CNDAC or azacitidine, as indicated in FIGS. 1A and 2A. The compound concentrations evaluated were HL-60 cells azacitidine $0.5 \times IC_{50} = 0.13$ µM; CNDAC $IC_{50} = 0.13$ µM: MV4-11 cells CNDAC $IC_{50} = 0.46$ µM. The cell cycle profiles were analysed after treatment under the indicated conditions.

Treatment with azacitidine alone caused an accumulation of cells in sub-G1, G2/M, and >G2/M seen at both 72 and 96 hours exposure (FIGS. 1A and 2A). CNDAC treatment alone caused an accumulation of cells in G2/M by 48 hours with a small induction of cells in sub-G1. The combination of agents showed a small additional increase in cells in sub-G1 with little change in the other cell cycle phases by 48 hours. By 72 hours, a more dramatic increase in sub-G1 representing 45% of the cells compared to 9% and 7% for the azacitidine and CNDAC single agent treatments respectively. Taken together these data suggest that the combination treatment causes a time dependent increase in cell death greater than either agent alone.

Annexin V Analysis

Figure 1B:
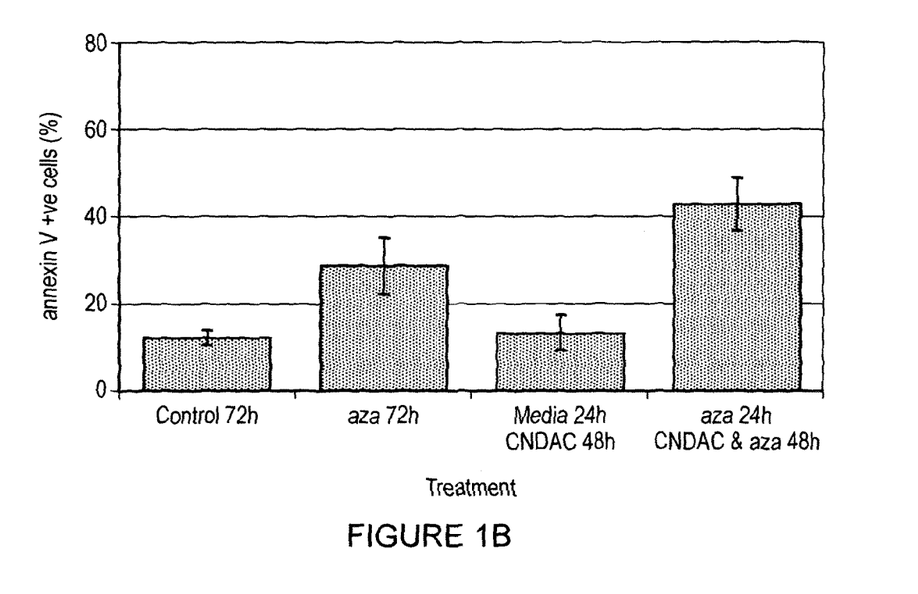
Figure 2B:
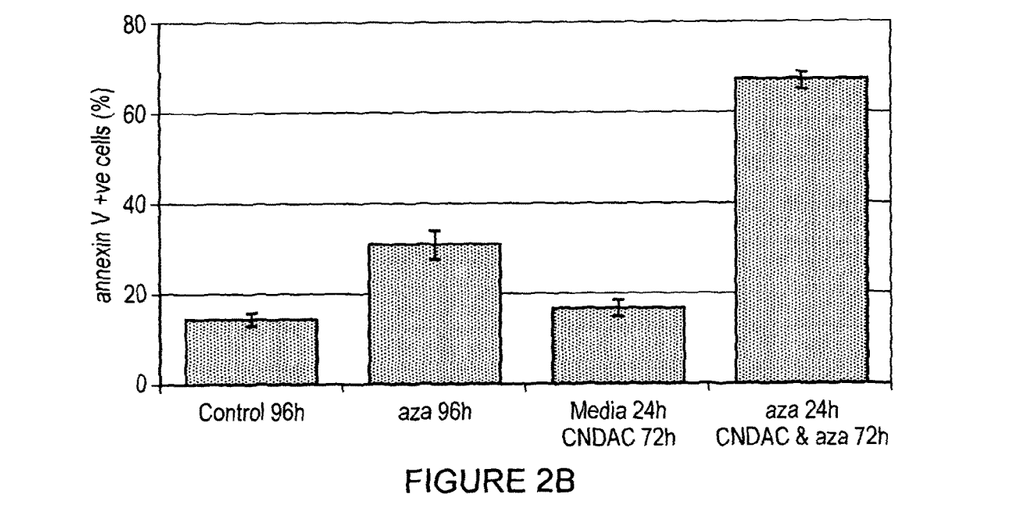

To evaluate the cell death in more detail, single agent and combination treatments of azacitidine and CNDAC in HL60s were measured by annexin V, a marker of apoptosis. Cells were exposed to azacitidine (128 nM) for a total of 96 hours. For the combination treatment after 24 hours, CNDAC (133 nM) was added for a further 72 hours in the presence of azacitidine. Single agent treatment with azacitidine caused a small increase in the proportion of apoptotic cells by 72 and 96 hours (FIGS. 1B and 2B). CNDAC alone showed little effect at either 48 or 72 hours compared to controls (FIGS. 1B and 2B). The combination of agents showed greater effects (66%) than either agent alone (azacitidine: 30.5% and CNDAC: 16.5%) with the greatest difference between single agents and the combination at the longest time point of 96 hours total treatment (FIG. 2B).

Western Blot Experiments

Figure 3:
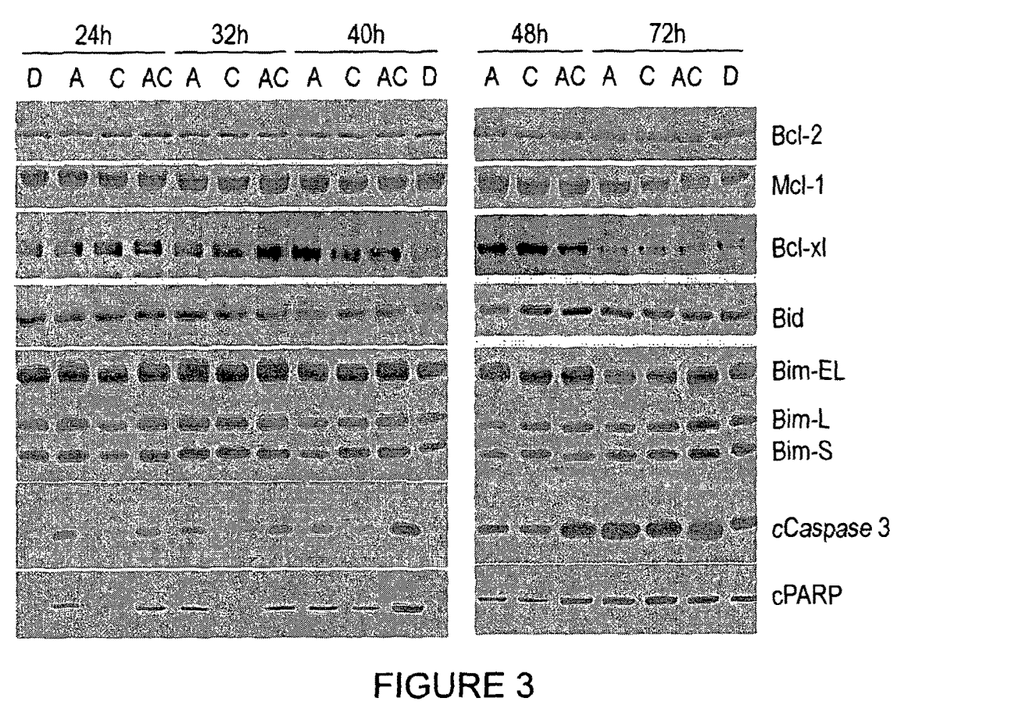
FIG. 3 shows a time course showing the effect of CNDAC and azacitidine alone or in combination on molecular events in HL60 cells. HL60 cells were treated as follows: mock treated with DMSO (D); treated with azacitidine only (0.5× $IC_{50}$: 128 nM) (A); treated with media for 24 hours followed by CNDAC (1×$IC_{50}$: 133 nM) (C); or azacitidine (128 nM) for 24 h followed by CNDAC (133 nM) (AC). Samples were collected at various times (indicated) after CNDAC addition. Cells were lysed, fractionated by SDS-PAGE, transferred to nitrocellulose and probed for cleaved PARP (a marker of apoptosis). Data is representative of two independent experiments.

In order to complement the cell cycle analysis, HL60 cells treated with the single agents or with the combination were assessed for induction of cleaved PARP (a marker of apoptosis) at a range of time points (FIG. 3).

HL-60 cells were treated with DMSO, 0.13 µM azacitidine, 0.13 µM CNDAC or both agents (AC). The schedule involved 24 h azacitidine or DMSO pretreatment followed by the addition of CNDAC or DMSO for the indicated times. Cells were harvested after 48 h-96 h total treatment time. The resulting lysates (20 µg) were resolved on 12% acrylamide Bis-Tris gels, transferred to nitrocellulose membranes and probed with the antibodies shown in FIG. 3. Results showed that treatment with azacitidine alone caused a small induction in cleaved PARP at early time points. Cleaved PARP was also seen in the combination treatment. At later time points, CNDAC also induced cleaved PARP at later time points. Treatment with the combination showed greater effects on cleaved PARP than either agent alone. The results indicate that the CNDAC and azacitidine combination induces apoptosis but does not modulate Bcl-2 family proteins.

Dosing Schedule for AML

In AML cell lines, the active metabolite of sapacitabine, CNDAC, is synergistic with hypomethylating agents and the synergy is more apparent if cells are treated with hypomethylating agents first.

A phase 1/2 study was carried out in order to evaluate the safety and efficacy of administering sapacitabine in alternating cycles with decitabine in newly diagnosed elderly AML. The decitabine dose is 20 mg/m$^2$ infused intravenously/day×5 consecutive days followed by 3-week rest for the first and odd number of cycles; the sapacitabine dose is 300 mg b.i.d.×3 days/week×2 weeks followed by 2-week rest for the second and even number of cycles. These doses are considered tolerable if DLT occurs in ≤2 of 6 patients in the Phase 1 part. The sample size for Phase 2 is 24 patients including those who have received the same doses of both drugs in the Phase 1 part because eligibility criteria are the same for both parts. The primary efficacy endpoint is response rate (CR, CRp, PR, or major HI). A secondary efficacy endpoint is median overall survival. The regimen will be considered tolerable if dose-limiting toxicity occurs in less than 33% of patients and the 8-week mortality is less than 37%. Eight-week mortality, or death rate, is defined as death due to any cause occurring within 60 days after the date of patient registration into the study.

Methods: Eligible patients must be ≥70 years with AML previously untreated for whom the treatment of choice is low-intensity therapy or the patient has refused standard induction chemotherapy; patients who received hypomethylating agents for prior MDS or MPD are excluded.

Results: 25 patients were treated with the above doses of decitabine and sapacitabine and 16 had ≥60 days of follow-up. Median age is 76. No dose-limiting toxicities were observed and the 8-week mortality rate was 12.0%. The response rate (CR, CRp, PR, or major HI) was 40%. Three patients achieved CR and 2 patients achieved PR and 1 patient achieved major HI in platelets. Time to response is 2-4 cycles. Eight patients have received ≥4 cycles of treatment. Three patients died within 60-days and the deaths were unrelated to study drugs by investigator assessment. Common adverse events (regardless of causality) included weakness, anorexia, nausea, diarrhoea, dehydration, dyspnea, edema, pneumonia, febrile neutropenia, neutropenia, thrombocytopenia, anemia, and hypocalcemia, most of which were moderate in intensity. These interim data suggest that this treatment regimen is safe and active in elderly AML.

Among a further 21 patients treated in a separate clinical study with an identical regimen and at least 60 days of follow-up, the rate of dose-limiting toxicity was 9.5% and the 8-week mortality rate was 14.3%. As above, the patients received intravenous decitabine at 20 mg/m$^2$ per day for five consecutive days of a 4-week cycle (odd cycles) and sequentially sapacitabine at 300 mg orally twice per day for three days per week for two weeks of a 4-week cycle (even cycles).

The 30-day death rate across all 46 patients treated with the regimen was 5%.

Various modifications and variations of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the relevant fields are intended to be covered by the present invention.

The invention claimed is:

1. A method of treating acute myeloid leukemia (AML) in a subject of 70 years of age or over, said method comprising administering to the subject a therapeutically effective amount of (i) sapacitabine, or a metabolite thereof; and (ii) decitabine; in accordance with a dosing regimen comprising at least one first treatment cycle followed by at least one second treatment cycle, wherein said first treatment cycle comprises administering a therapeutically effective amount of decitabine for 5 consecutive days followed by a rest period of from 3 to 5 weeks, or until treatment-related toxicities are resolved, whichever is longer; and wherein said second treatment cycle comprises administering a therapeutically effective amount of sapacitabine, or a metabolite thereof, in a dose of about 100-400 mg b.i.d. for 3 consecutive days per week, for 2 weeks followed by a rest period of from 2 to 4 weeks, or until treatment-related toxicities are resolved, whichever is longer.

2. A method according to claim 1 wherein the second treatment cycle comprises administering a therapeutically effective amount of sapacitabine.

3. A method according to claim 1 wherein the metabolite of sapacitabine is 1-(2-C-Cyano-2-deoxy-β-D-arabino-pentafuranosyl)-cytosine (CNDAC).

4. A method according to claim 1, wherein said first treatment cycle comprises administering a therapeutically effective amount of decitabine for 5 days followed by a 3 week rest period.

5. A method according to claim 1, wherein said second treatment cycle comprises administering a therapeutically effective amount of sapacitabine or metabolite thereof for 3 consecutive days per week, for 2 weeks followed by a 2 week rest period.

6. A method according to claim 1, which comprises two or more of each treatment cycle.

7. A method according to claim 6, which comprises two to four of each treatment cycle.

8. A method according to claim 1, wherein the decitabine is administered intravenously.

9. A method according to claim 1, which comprises three or more of each treatment cycle.

10. A method according to claim 1, which comprises four or more of each treatment cycle.

11. A method according to claim 1, which comprises five or more of each treatment cycle.

12. A method according to claim 1, wherein the decitabine is administered in a dose of from about 10 to about 20 mg/m².

13. A method according to claim 12, wherein the decitabine is administered in a dose of about 20 mg/m² per day.

14. A method according to claim 1, wherein the sapacitabine or metabolite thereof is administered orally.

15. A method according to claim 14, wherein the sapacitabine or metabolite thereof is administered in a dose of about 250-300 mg b.i.d.

16. A method according to claim 14, wherein the sapacitabine or metabolite thereof is administered in a dose of about 300 mg b.i.d.

17. A method according to claim 1, wherein the patient is 75 years of age or over.

18. A method of treating acute myeloid leukemia (AML) in a subject of 70 years of age or over, said method comprising administering to the subject a therapeutically effective amount of (i) sapacitabine; and (ii) decitabine; in accordance with a dosing regimen comprising at least one first treatment cycle followed by at least one second treatment cycle,
wherein said first treatment cycle comprises administering decitabine intravenously in a dose of about 20 mg/m² per day for 5 consecutive days followed by a 3 to 5 week rest period, or until treatment-related toxicities are resolved, whichever is longer; and
wherein said second treatment cycle comprises administering sapacitabine orally in a dose of about 300 mg b.i.d. for 3 consecutive days per week, for 2 weeks followed by a 2 to 4 week rest period, or until treatment-related toxicities are resolved, whichever is longer.

19. A method of treating acute myeloid leukemia (AML) in a subject of 75 years of age or over, said method comprising administering to the subject a therapeutically effective amount of (i) sapacitabine; and (ii) decitabine; in accordance with a dosing regimen comprising at least one first treatment cycle followed by at least one second treatment cycle,
wherein said first treatment cycle comprises administering decitabine intravenously in a dose of about 20 mg/m² per day for 5 consecutive days followed by a 3 to 5 week rest period, or until treatment-related toxicities are resolved, whichever is longer; and
wherein said second treatment cycle comprises administering sapacitabine orally in a dose of about 300 mg b.i.d. for 3 consecutive days per week, for 2 weeks followed by a 2 to 4 week rest period, or until treatment-related toxicities are resolved, whichever is longer.

20. A method of treating acute myeloid leukemia (AML) in a subject of 75 years of age or over, said method comprising administering to the subject a therapeutically effective amount of (i) sapacitabine, or a metabolite thereof; and (ii) decitabine; in accordance with a dosing regimen comprising at least one first treatment cycle followed by at least one second treatment cycle,
wherein said first treatment cycle comprises administering a therapeutically effective amount of decitabine for 5 consecutive days followed by a rest period of from 3 to 5 weeks, or until treatment-related toxicities are resolved, whichever is longer; and
wherein said second treatment cycle comprises administering a therapeutically effective amount of sapacitabine, or a metabolite thereof, in a dose of about 100-400 mg b.i.d. for 3 consecutive days per week, for 2 weeks followed by a rest period of from 2 to 4 weeks, or until treatment-related toxicities are resolved, whichever is longer.

21. A method of treating acute myeloid leukemia (AML) in a subject of 70 years of age or over, said method comprising administering to the subject a therapeutically effective amount of (i) sapacitabine, or a metabolite thereof; and (ii) decitabine; in accordance with a dosing regimen comprising at least one first treatment cycle followed by at least one second treatment cycle,
wherein said first treatment cycle comprises administering a therapeutically effective amount of decitabine for 5 consecutive days followed by a rest period of from 3 to 5 weeks, or until treatment-related toxicities are resolved, whichever is longer; and
wherein said second treatment cycle comprises administering a therapeutically effective amount of sapacitabine, or a metabolite thereof, in a dose of about 100-400 mg b.i.d. for 3 consecutive days per week, for 2 weeks followed by a rest period of from 2 to 4 weeks, or until treatment-related toxicities are resolved, whichever is longer;
and wherein said dosing regimen comprises two or more of each treatment cycle.

* * * * *